United States Patent [19]

Parsons et al.

[11] Patent Number: 5,747,265
[45] Date of Patent: May 5, 1998

[54] METHOD FOR MEASURING THE AMOUNT OF A CELL-ASSOCIATED MOLECULE

[75] Inventors: George H. Parsons, Arlington; Margaret A. Johns, Waltham, both of Mass.; Arthur E. Rugg, Londonberry, N.H.

[73] Assignee: T Cell Diagnostics, Inc., Cambridge, Mass.

[21] Appl. No.: 62,442

[22] Filed: May 14, 1993

Related U.S. Application Data

[63] Continuation-in-part of Ser. No. 968,793, Oct. 30, 1992, abandoned.
[51] Int. Cl.$^6$ .................................................. G01N 33/53
[52] U.S. Cl. ................................. 435/7.2; 435/7.24
[58] Field of Search ........................... 435/6, 7.1, 7.2, 435/7.24; 935/77, 78, 81, 7.24

[56] References Cited

U.S. PATENT DOCUMENTS

| | | | |
|---|---|---|---|
| 4,752,562 | 6/1988 | Sheiman et al. | 435/5 |
| 5,149,624 | 9/1992 | Gabriel | 435/6 |

OTHER PUBLICATIONS

TRA$_x$ Total Receptor Assay Pamphlet, T Cell Diagnostics Inc. "An Enzyme Immunoassay for the Quantitative Measurement of Total CD4 Protein and for the Enumeration of CD4 T Lymphocytes in Human Peripheral Blood Specimens", Product Brochure of T Cell Diagnostics, Inc., Cambridge, MA (1993).

Jones, G.R. et al., Poster Abstract Presentation Number: 33 "Dried Blood Spot (DBS) Screening: Effect of Reduced DBS Elution Times on Antibody Detection in OTC's HIV Antibody Elisa Tests", VIIIth Annual ASTPHLD Conference on Human Retrovirus Testing, Atlanta, Georgia (Mar. 3–5, 1993).

Schleicher & Schuell Brochure, Product Brochure of Schleicher & Schuell, Keene, NH 03431 (1993).

Gicquelais et al., J. Clin. Microbiol., 28(11)(1990), pp.2485–2490. See the Life Sciences Collection Abstract:1548087.

Tomlinson, BioTechniques, 13(5), (1992), pp. 710–711. See the DBA Abstract Acc. No. 92–13918.

Yourno et al., J. Clin. Microbiol., (Nov. 1992) pp. 2887–2892, vol. 30, No. 11.

Gonzalez et al. (1990) Clin. Chem. 36/9:1667–1672.

Huang et al. (1990) Hum. Genet. 84:129–131.

Biervliet et al. (1982) Clinica Chimica Acta 120:191–200.

Cassol et al. (Dec. 1992) J. Clin. Micro. 30(12):3039–3042.

Lyonnet et al. (Aug. 27, 1988) Lancet II, 507.

Williams et al. (Sep. 17, 1988) Lancet II 687.

Obregon (1982) Ann Clin Biochem 19:29–34.

Larsen et al. (1976) J. Clin Endocrinol Metab. 42:987–990.

Hata et al. (1983) Clin Chem 29(7): 1437–1440.

*Primary Examiner*—Lisa B. Arthur
*Attorney, Agent, or Firm*—Law Offices of Jane Massey Licata

[57] ABSTRACT

The invention is directed to methods and a device for detecting or measuring the amount of a cell-associated molecule in a biological fluid sample. Cell-associated molecules which can be detected or measured include, but are not limited to, cell surface antigens, intracellular cytokines, microbial antigens, pharmacological agents or their metabolites, and nucleic acids. In the preferred embodiment, a sample of whole blood is collected on filter paper and dried. A dot is punched form the dried blood spot and the analyte of interest eluted from the paper with a buffered, relatively highly concentrated detergent solution. The eluate is then assayed in a standard assay, such as an immunoassay.

12 Claims, 2 Drawing Sheets

METHOD FOR MEASURING THE AMOUNT OF A CELL-ASSOCIATED MOLECULE

This application is a continuation-in-part of Ser. No. 07/968,793, filed Oct. 30, 1992 now abandoned.

BACKGROUND OF THE INVENTION

There are a number of cell-associated molecules including cell surface antigens, intracellular cytokines, microbial antigens, pharmacological agents and their metabolites, and nucleic acids.

Cytokines

Cytokines are a large, diverse group of bioactive proteins and peptides generally having relatively low molecular weights which regulate a large number of cellular activities. For example, cytokines regulate immunoglopbulin production by B lymphocytes and the biosynthetic activities of various cell types. Interleukin-2 (IL-2), originally discovered as a T-cell growth factor, and other immunologically active cytokines are associated with T-cell function and with the growth and differentiation of a variety of hematopoietic cell types.

Cytokines are generally produced in a non-constitutive manner, usually requiring activation or stimulation of the producing cell, presumably through a cell-surface receptor. While many of the better characterized cytokines are produced by the cells of the immune system, cytokines are also produced by a wide variety of cell types. Typically, a given cell type produces a number of different cytokines. Cytokines have been implicated in a wide variety of immune and inflammatory responses. Their actions are organized in complex interacting networks, wherein the release of one cytokine may lead to a diverse array of physiological responses, some due to the induction of yet other cytokines.

The vast majority of research on cytokine production and action was performed using in vitro culture systems. In fact, most cytokines are not detectable in the blood stream, even during an immune response. Because cytokines active in immune responses appear to have been designed to act over a short range and a short time interval, they are generally active at very low concentrations. Most cytokine research is based on measurement of the biological activity of cytokines in various bioassays. Cytokine levels in blood have been measured in immunoassays, such as enzyme-linked immunosorbent assay (ELISA). This approach, however, suffers from several limitations when used to detect cell derived cytokines in serum because of their low concentrations and extremely short half lives in vivo. The detectability of cytokines in serum by ELISA with monoclonal antibodies is affected by several factors such as: 1) locally produced cytokine in vivo is quickly absorbed by target cell receptors and may never reach the plasma; 2) a cytokine's short half-life makes the sampling time critical; and 3) cytokine proteins are usually unstable during sample storage. In general, immunoassays of molecules present in serum are not useful for detecting proteins that do not survive storage. For all the foregoing reasons, there is a need for improved methods to detect and measure cytokines in blood samples.

Microbial Antigens

Some of the most successful microorganisms multiply in, or on the surface of, epithelial cells at the site of entry into the body, resulting in a spreading infection in the epithelium, followed by shedding to the exterior. For example, viral infections are generally confined to epithelial surfaces including Influenza, Parainfluenza, Rhinoviruses, Coronaviruses and Papillomas.

There is a need in the art for a simple, direct and sensitive method for detecting the presence of a microorganism invading the epithelium by detecting or measuring the amount of a molecule or antigen associated with the virus in an epithelial cell, tissue or fluid sample.

Some of the more important viruses regularly establish systemic infections after traversing epithelial surfaces. These include intracellular microorganisms. For obligate intracellular microbes to spread systemically, they must first enter the blood or lymph. This means they must gain access to the lumen of a subepithelial lymphatic or blood vessel as a free organism, or first enter a mobile cell (such as a leukocyte) which is carried through the blood or lymph. Examples of organisms which infect leukocytes include measles and small pox viruses. Such organisms multiply inside the cell while avoiding the intracellular defense mechanisms, such as lysosomal degradation.

It would be of great benefit if it were possible to detect and quantify various pathogenic microorganisms in a simple, direct and sensitive assay of a body fluid containing the organism or host cells harboring the organism with minimal handling and processing of the sample. The present invention is intended to provide such assays.

Nucleic Acids

The amount of DNA (deoxyribonucleic acid) or RNA (ribonucleic acid) in a cell is a useful marker for the presence of certain cell-associated molecules. Additionally, detection of DNA or RNA may be useful for determining the presence of malignant or pre-malignant cells. Normal cells have only a single copy of cellular DNA whereas malignant cells are often polyploid. Conventionally, polyploidy is assessed by flow cytometric analysis of total cellular DNA using DNA binding dyes. The present invention allows a laboratory lacking a flow cytometer to detect polyploidy or measure the amount of DNA or RNA in a cell by direct assay, thus providing a way of detecting various components, and even tumor cells in a cellular sample.

Cell Surface Antigens

A multitude of molecules, including proteins, glycoproteins, glycolipids, oligosaccharides, and the like are expressed on cell surface membranes. Also detectable, either on the surface, or in the intracellular compartment of a cell, are molecules produced by intracellular parasites, such as viruses. Cell surface molecules are also present in the cytoplasm. Conventional flow cytometry assays detect or enumerate cells expressing a given molecule on their surface by visualizing or measuring the binding of an antibody to an epitope of that molecule on the cell. Well known cell surface molecules with clinical significance include T-cell receptor molecules. Many such molecules are defined by their reactivities with particular monoclonal antibodies (Mabs). In particular, identification and enumeration of T-cells expressing CD4 and CD8 molecules has been of great clinical utility. Indeed, following the circulating levels of CD4+ cells is a key prognostic indicator for evaluating progression of Acquired Immunodeficiency Syndrome (AIDS).

The two main subsets of T cells are known as CD4 and CD8 and are distinguished by their regulatory function, helper/inducer and suppressor/cytotoxic, respectively. The CD4 molecule is a glycoprotein monomer of approximately 55 kilodaltons with extracellular, transmembrane and cytoplasmic regions. The CD4 molecule can function to transduce intracellular signals and to modulate T cell activation which results in signaling of B cells and induction of CD8+ T cells to become cytotoxic by cytokine release. Also, CD4 may serve as an adhesion molecule in support of anchoring the MHC class II molecule, or antigen presenting cells, with the T cell receptor. As such, the CD4 molecule serves as the phenotypic marker for helper T lymphocytes.

In general, the identification of human B and T lymphocyte subsets by cell surface markers has enabled profiles of immune status to be developed for normal as well as pathological conditions. For instance, the cell surface antigens CD19, CD20 and CD21 are found in greater than 90% of blood B lymphocytes, while CD2 and CD3 are expressed on nearly all T lymphocytes in normal peripheral blood. T lymphocytes, which are responsible for cell mediated immunity, can be further differentiated into two subsets depending on their phenotype, receptor specificity for MHC and cellular function. Generally, the CD4+ CD8– helper T lymphocytes comprise approximately 65% of peripheral T cells and are able to secrete cytokines upon antigen activation in association with MHC class II molecules. Another subset, the CD4-CD8+ cytotoxic lymphocytes (about 35% of peripheral T cells) are able to lyse target cells after activation by MHC class I presented antigens.

By using monoclonal antibody reagents to these various cell surface markers in conjugation with flow cytometric methods it has been possible to monitor the changing composition of lymphocyte subsets in peripheral blood associated with various autoimmune and immunodeficiency diseases, leukemias and lymphomas, and transplantation rejection. In the case of AIDS, it has been established that the CD4 molecule is the cell surface receptor for the human immunodeficiency virus (HIV) and it has been shown possible to monitor the depletion of CD4 T lymphocytes which are characteristic of progression to AIDS.

Early methods for assaying lymphocyte subsets such as by placque and cell-mediated functional assays were highly technique dependent and not cell lineage specific. With the availability of monoclonal antibodies against cell surface markers, the measurement of cell surface CD4 by flow cytometry has expanded the study of lymphocyte subset identification for immune monitoring. However, this method requires the use of complex procedures, expensive instrumentation and is labor intensive. TRAx™ CD4, is an enzyme immunoassay by which total CD4 protein may be determined from a whole blood lysate. The results obtained using this micotiter based enzyme-immunoassay (EIA) correlate at greater than 88% with CD4 T lymphocyte counts as determined by flow cytometry.

The dried blood spot (DBS) specimen collection medium has proven to be a valuable method for epidemiological studies. Neonatal heel stick specimens are collected routinely and have been shown to be a useful for the detection of PKU and hypothyroidism, sickle-cell anemia and other hemoglobinopathies, and HIV. In developing countries, adult finger stick DBSs have provided a way to sample populations and transport stable specimens to the testing laboratories. However, this technique has not heretofore been applied to techniques for determining cell-associated molecules which are contained within the cell or on the cell surface. Until now, a dried blood collection method has not been used for the determination of CD4 lymphocytes in blood.

SUMMARY OF THE INVENTION

Methods of assaying for cell associated molecules are provided. In one embodiment, a sample of whole blood is assayed for the total amount of a selected cell-associated molecule, CD4. In a specific embodiment, a blood sample is spotted onto filter paper, the filter paper dried and placed in a vial containing a selected diluent and lysis reagent, and incubated for a selected period of time at a selected temperature. A sample of a selected size is then recovered from the vial and assayed in a standard CD4 assay. Cell associated molecules may also preferentially include CD8, CD3, CD19, CD25 (IL-2R), CD2, CD56, CD54 (ICAM-1), intracellular microbial pathogens, cytokines and nucleic acids. Cell associated molecules are found either within the cell or on the cell surface, as opposed to soluble molecules. A device for use in the assay of the invention is also provided.

DETAILED DESCRIPTION OF THE INVENTION

The present invention is directed to the detection or measurement of the total amount of a molecule (hereinafter "target molecule") in a sample and the use of such detection or measurement in the detection, diagnosis, staging, determination of severity, and therapy of diseases and disorders, and in the enumeration of cells expressing the target molecule. The methods and device of the invention allows detection or measurement of target molecules heretofore not readily accessible for detection by binding to a binding partner such as an antibody.

Any target molecule for which a binding partner is available can be detected or measured according to the present invention. The target molecule may be endogenous (a molecule that is encoded by the genome of the host cell or is produced by the host cell). Examples of endogenous target molecules include cytokines, cell adhesion molecules, phenotypic markers, activation markers, and nucleic acids.

The target molecule may also be an exogenous molecule (a molecule encoded by a genome not of the host cell or otherwise produced by an exogenous agent). Typical exogenous target molecules which may be measured according to the present invention are molecules associated with microbial pathogens such as viral antigens.

Non-limiting examples of target molecules for which the present invention is intended to apply are proteins, peptides, glycoproteins, glycopeptides glycolipids, polysaccharides, oligosaccharides, nucleic acids, pharmacological agents and their metabolites, and the like, or fragments thereof. Preferred target molecules according to the present invention are microbe- associated molecules, cytokines, adhesion molecules, pharmacological agents or their metabolites, and the like. In a specific embodiment, the invention provides a method for detecting or measuring the total amount of a target molecule which is intracellular. In another embodiment, the target molecule is a cell surface molecule. As used herein, by cell-associated molecule" is meant that the molecule is attached to the cell surface or is intracellular.

Depending on the sample and nature of the target molecule, the measurement of a total amount of target molecule can substitute for direct enumeration of cells expressing the target molecule and can be valuable in monitoring the effect of a therapeutic on a subject, detecting, diagnosing or staging a disease in a subject, and predicting therapeutic outcome or disease prognosis and in evaluating and monitoring immune status of patients.

Binding partners for use in the assays of the invention include, but are not limited to, receptors for and antibodies to the target molecules. In particular, binding partners which are not antibodies include cell surface receptors for the target molecules.

In a preferred embodiment, the target molecule is an antigen, and detection or measurement of the target molecule is carried out by a method of immunospecific binding of the target molecule to at least one antibody. All antigens which carry an antigenic determinant or epitope which can be detected or quantitated in an immunoassay are intended to be within the scope of the present invention.

A preferred subject from which one may obtain samples for the methods of the present invention is a vertebrate, including but not limited to, a mammal, fish, amphibian, reptile, bird, marsupial and most preferably, a human. Thus, the methods of this invention are applicable to human clinical and veterinary uses.

As used herein, a "sample" refers to a collection of cells in the milieux in which they wee obtained, i.e., a biological fluid, or to membrane and/or intracytoplasmic components of the cells. Total molecules may be measured in samples derived from a biological fluid, e.g., whole blood, plasma, serum, blood cells, saliva, urine, synovial fluid, pleural effusions, tumor and tissue infiltrates, amniotic fluid, spinal fluid or cranial fluid. In another embodiment, the biological fluid may be cell culture fluid. The sample can comprise tissue, including interstitial fluid. Preferably, when the sample is a tissue sample, the tissue is treated to disrupt the connective tissue matrix, e.g., by trypsin digestion or homogenization. In another embodiment, the sample comprises cells derived from the foregoing sources. In the most preferred embodiments, the sample comprises whole blood. The amount of sample used is a function of the type of target molecule and its abundance in the preparation, and can be determined by one of ordinary skill in the art without undue experimentation.

The method provided by the present invention, as described in more detail below, overcomes many of the limitations of prior art methods, and in particular, with regard to the measurement or detection of cell associated molecules, which heretofore required cell isolation followed by direct or indirect immunofluorescence analysis by microscopy or flow cytometry. Limitations of the prior art procedures included the requirement for fresh sample, fairly large sample size, enriched cell populations rather than whole tissue or blood, extensive preparation time and expensive equipment such as a flow cytometer. The methods provided herein overcome these limitations. Surprisingly, the methods and device as taught herein are suitable in assaying various components of fresh samples, i.e. whole blood, and in relatively low volumes of samples, i.e. about 20-100 µ l. Thus, sample collection involves techniques as simple as a fingerstick. The samples are then stable enough to be transported by mail or otherwise, to a central site for analysis, thus eliminating the need for fresh blood samples and phlebotomy.

In the method steps of the presently claimed invention, a selected amount of a liquid biological sample is spotted onto a filter paper collection device. By spotted is meant that the sample is contacted with such filter paper collection device, transferring all or a portion thereof to the device. Filter paper suitable for purposes herein are those generally known to the art and commercially available. Various grades are generally available and relate to the porosity of the paper, as well as its absorbency, consistency and the material it is made out of. One skilled in the art should optimize these parameters to achieve overall evenness of the sample dispersion across a defined area of the filter paper, so that when a dot is punched out, the concentration of the sample will be relatively uniform on a sample to sample basis. In certain preferred embodiments, for example when leukocyte markers are the target molecules in a whole blood sample, filter paper comprising 100% cotton fibers is preferred. In this scenario, mean serum uptake of about 1.4 to about 1.7 µ per filter paper spot, with about 1.5 to about 1.6 µ l is particularly preferred. Serum uptake is a conventional measurement of absorbance, and thus absorbency may be determined and optimized using this technique. It is generally preferred that absorption time be within about one minute, with 5-30 seconds more preferred. Consistency may be measured by wicking time and evenness of flow. Porosity relates to both absorbing and consistency, as the pore size and pore distribution of the paper affects these aforementioned parameters. In certain embodiments, synthetic fabrics, both woven and nonwoven, such as polyester, or Gortex™ may offer advantages in overall assay performance.

Amounts of sample suitable for this purpose are relatively small, that is to say that amounts ranging from about 150 microliters to about 10 microliters are preferred, with about 80 microliters to about 40 microliters particularly preferred. The sample so transferred is preferentially allowed to dry under room temperature conditions that may generally range from about 18° C. to about 29° C., with about 20° C. to about 26° C. being more typical, or at about 30° C. to 37° C. for a lesser period of time, if long-term stability of the sample is not required. This drying step is generally from about one to four hours. At this point, the sample may be stored until it is appropriate for further analysis, or may be immediately subjected to further handling as provided herein. The dried sample may be sent to a central testing facility for such further handling, or may be subjected to such steps on the site the sample was taken.

A suitable amount of the dried sample is removed from the spotted area and contacted with a selected diluent combined with a lysis reagent for a period of time sufficient to solubilize said sample. In general, a ¼ inch diameter dot holds approximately 12 µ l of sample, which may be a suitable sample size for certain assay conditions, while more or less may be required for other assays. One skilled in the art may determine their needs in this regard through routine optimization. For example, smaller dots could be used for analytes of relatively low concentrations, i.e. less than about $10^{-11}$, while multiple dots (about 5.5 mm in diameter) could be used for higher concentrations, i.e. greater that about $10^{-11}$. By "solubilize" is meant that solid portions of the biological sample (i.e. intact cells) are lysed, allowing the target molecules to be released into the diluent and lysis reagent. In preferred embodiments, this period of time is at least about two hours, at room temperature. Suitable diluents include physiologically compatible buffers, such as phosphate-buffered saline, saline, Dulbecco's Media, and the like. A particularly preferred buffer comprises phosphate buffered saline, preferably supplemented with at least one protein, such as a bovine-derived serum protein. suitable lysis reagents comprise at least one non-ionic detergent. Of these may be mentioned non-ionic detergents in the Triton series such as Triton X-100, X-114, X-305, X-405, those of the Brij series such as Brij 35, 56, 58, those of the Tween series, such as Tween 20, Tween 80, Nonidet P-40 (NP40), and zwitterionic detergents such as CHAPS and CHAPSO, and the like. Preferred for use herein is a combination of Triton X-100 and NP40, in relatively high concentrations. Preferred concentrations for contact with the sample range form about 6–10% and 4–7%, respectively, with about 9% and 6%, respectively, particularly preferred when leukocyte markers are the target molecule (all measured on a concentration basis that is not a final concentration when considering the dilution factor of the liquid sample). The solubilized sample may be processed further in accordance with the method taught herein or stored until further handling is desired, and when stored, preferably frozen at least about −20° C., with about −20° C. to at least about −70° C. more preferred, and at least about −70° C. particularly preferred.

A selected amount of said sample so solubilized is collected and contacted with at least one binding partner specific for the target molecule sought to be detected or enumerated. This step may be performed in accordance with well-accepted immunoassay detection kits and the like for this purpose. As an example, in the case of analysis for detection of the CD4 receptor, a TRAx™ CD4 Assay Kit, available from T Cell Diagnostics, Inc., Cambridge, Mass., may be utilized for this purpose by following the assay protocol provided with that kit.

This may be accomplished with other such conventional assay techniques or even commercially available assay kits for the assay of other cell surface receptors and the like.

In a preferred embodiment, capillary or venous blood samples are collected on filter paper and dried. A suitable area is taken from the dried blood spot, for example, a 5.5 mm (0.25 inch) dot is punched from the dried blood spot and the analyte eluted from the paper with a buffered detergent solution for at least 2 hours at room temperature.

Fifty microliters (50 µl) of the eluate is then assayed in a standard TRAx™ CD4 microtiter plate ELISA assay which is intended for the determination of CD4 cell counts in liquid blood samples. Assay Cvs are less than 8% for both intra and inter assay. Assay sensitivity is about 86–130 cells/µ l, and particularly 86 cells per pl, and correlation with flow cytometry is approximately 90%. Samples are stable for several months when stored with desiccant at 4° C. The solubilized sample may also be stored frozen after detergent treatment, for example at −20° C., preferably at −70° C. This has the advantage of allowing the concurrent analysis of multiple samples taken at different times in a single assay, thus reducing interassay variability. The methods of the invention show great promise in areas where access to flow cytometry is limited.

The filter paper collection device of the invention may be provided in a separate packaged format suitable for "in field" retrieval of biological samples. Also provided will be a container to retain the sample once the paper is spotted, which helps to contain the possible infectivity of the sample. Additionally, either in conjunction with the filter paper collection device or separately, the remaining reagents useful for the practice of the present invention can be conveniently provided in a kit. the essential elements of this portion of a kit of the invention are a concentrated non-ionic detergent solution and a means for immunologically detecting the presence of an antigen.

The kit can comprise any immunological detection means known in the art, i.e. sandwich assay formats, competitive immunoassay formats, and the like. Preferably, the immunological detection means are a first capture antibody specific for the cell-associated molecule, and a second detectable antibody specific for the cell-associated molecule. The first antibody can be provided on a solid support, such as a glass or plastic bead, membrane, a plastic stick, a microwell, a glass or plastic test tube, or other solid supports known in the art for immunoassays. Alternatively, the first antibody can be provided for later immobilization. The first and second antibodies can be provided as a lyophilized preparation for reconstitution, or as a concentrated solution. The second antibody can be detectable by labeling means. In a preferred embodiment, the labeling means is an enzyme.

The detergent solution is provided in a container having sufficient volume to hold the amount of solution necessary for the number of assays contemplated by the kit. Preferably, the detergent solution comprises two or more non-ionic detergents. In a preferred embodiment, the detergent solution comprises 9% Triton X-100 and 6% N-40 in distilled water. That particular detergent concentration is optimum with respect to an assay for both CD4 and CD8.

Preferably, the kit comprises a cell-associated molecule standard, either in solution or lyophilized for reconstitution. More preferably, the kit comprises a standard comprising a known number of cell positive for the molecule of interest. Thus, the activity in an assay for the cell-associated molecule in an unknown sample can be directly compared with a known sample, and the number of cells in the unknown sample that are positive for the molecule enumerated thereby.

The kit can further comprise a reagent reactive with label, when the second antibody is detectable by attachment of a label to the antibody. For example, when the label is an enzyme, the kit can provide the enzyme substrate. The kit can also provide a dilution buffer, in final concentration, high concentration for dilution or dry for reconstitution.

In yet a further embodiment, a kit provides immunological detection means for more than one molecule. In a preferred embodiment, the kit comprises immunological detection means for both CD4 and CD8 antigens.

The invention is further illustrated by the following, non-limiting examples.

EXAMPLES

Example 1

Assay Protocol

After a skin puncture or finger prick, whole blood is spotted onto Schleicher and Schuell, Inc. (Keene, N.H.) grade 903 filter paper. Circular marks are filled with about 60 µl of blood. The paper is dried for about two hours at room temperature and either used immediately or stored with a desiccant, in a closed container at about 4° C.

A 0.25 inch dot is punched from a dried blood spot and placed into a 12×75 mm glass tube. 100 µl of Eluting Buffer is added. The Eluting Buffer is a 6:1 solution of TRAx™ CD4 Sample Diluent (T Cell Diagnostics, Inc; Cambridge, Mass.) and TRAx™CD4 Lysis Reagent (T Cell Diagnostics, Inc; Cambridge, Mass.) e.g., 1.0 ml Sample Diluent (a buffered solution with bovine-derived serum proteins and thimerosal) plus 0.2 ml Lysis Reagent (6% Nonidet P-40 (NP-40) and 9% Triton X-100 in 1X PBS). The glass tube is then covered and placed on a shaker st 200 rpm for at least 2 hours at room temperature. At the end of this period, 50 μl is removed from the glass tube after carefully squeezing the dot with the tip of the pipette and mixing the solution. The 50 μl sample is added to a standard TRAx™ CD4 assay following the protocol in the TRAx™ CD4 Assay Kit insert (T Cell Diagnostics, Inc; Cambridge, Mass.).

Example 2

TRAx™ CD4 Assay

The TRAx™ CD4 Assay is a sandwich EIA for the quantitative measurement of total CD4 protein and for the enumeration of CD4 lymphocytes in human blood. Results obtained using this assay have been demonstrated to correlate to absolute CD4 T lymphocyte counts as determined by flow cytometry combined with hematological data. A simple pretreatment of whole blood specimens release the CD4 protein from the lymphocytes. Specimens can then be assayed by EIA and/or stored at −20° C. to −70° C. for later study. The assay is performed in microtiter wells which have been pre-coated with monoclonal antibody to human CD4 protein. A second anti-CD4 monoclonal antibody conjugated to horseradish peroxidase is pipetted into the wells, followed by standards, controls or specimens. The solubilized CD4 protein present in the standards, controls or specimens binds to the antibody coated on the plate while the conjugated antibody binds to a second epitope on the CD4 molecule completing the sandwich. After an incubation period, the wells are washed thoroughly to remove unreacted components and an enzyme-specific chromogen solution is added. After an additional short incubation, the reaction is terminated and the absorbance at 490 nm measured. The colored endpoint which results is directly proportional to the amount of CD4 protein present and is equivalent to the number of CD4 T lymphocytes in the original specimen. A standard curve is prepared from standards and control and specimen values are determined from the standard curve and reported as cells/μl.

Example 3

CD4 TRAx™ Paper Dot Assay-Spike and Recovery

Five fresh whole blood samples were collected in EDTA and one half of the volume of each sample was depleted of CD4. This was used to dilute the remaining half of the sample so as to create the addition of a known amount of CD4, when measured. The addition was at four different concentrations. These were spotted on S&S 903 filter paper according to the procedure described in Example 1, as well as the high specimen (neat) and depleted portions of the sample. The dilutions performed cover the range of the standard curve. The assay is performed according to the procedures described in the foregoing examples. The recoveries were calculated based on the amount of recovered divided by the amount added (determined from the neat and depleted values). Results are shown in Table 1. The recovery for the addition of a known amount of CD4 into five separate fresh whole blood spotted samples over the range of the standard curve averaged 98%.

TABLE 1

| SAMPLE | CD4 ADDED U/Ml | RECOVERED CD4 U/Ml | % CD4 RECOVERED | AVERAGE RECOVERY |
|---|---|---|---|---|
| 929 | 80 | | | |
| 1:1.5 | 54 | 52 | 96 | 101% |
| 1:2 | 43 | 46 | 107 | |
| 1:3 | 31 | 31 | 100 | |
| 1:4 | 24 | 24 | 100 | |
| 0 | 6 | | | |
| 931 | 82 | | | |
| 1:1.5 | 56 | 54 | 96 | 92% |
| 1:2 | 43 | 41 | 95 | |
| 1:3 | 30 | 27 | 90 | |
| 1:4 | 23 | 20 | 87 | |
| 0 | 4 | | | |
| 932 | 101 | | | |
| 1:1.5 | 69 | 65 | 94 | 94% |
| 1:2 | 53 | 49 | 92 | |
| 1:3 | 38 | 35 | 92 | |
| 1:4 | 29 | 29 | 100 | |
| 0 | 6 | | | |
| 933 | 64 | | | |
| 1:1.5 | 44 | 44 | 100 | 105% |
| 1:2 | 34 | 36 | 106 | |
| 1:3 | 24 | 25 | 104 | |
| 1:4 | 19 | 21 | 110 | |
| 0 | 4 | | | |
| 934 | 92 | | | |
| 1:1.5 | 63 | 64 | 102 | 97% |
| 1:2 | 50 | 46 | 92 | |
| 1:3 | 36 | 32 | 89 | |
| 1:4 | 28 | 29 | 104 | |
| 0 | 7 | | | |

Example 4

CD4 TRAx™ Paper Dot Assay-Linearity

Eleven fresh whole blood samples were collected in EDTA and spotted onto S&S 903 filter paper according to the procedure described in Example 1. A portion of each sample was saved for flow determinations and for lysate preparation. The dilutions performed on the spots cover the range of the standard curve. The assay is performed according to procedures described in Examples 1 and 2. The recoveries are calculated based on the neat value. Results are shown in Table 2. The recovery for parallel dilution of eleven fresh whole blood spotted samples over the range of the standard curve averaged 112%.

TABLE 2

| SAMPLE | DILU-TION | U/Ml MEAS-URED | U/Ml CO-RRECTED | RECOV-ERY | AVERAGE RECOVERY |
|---|---|---|---|---|---|
| 761 | NEAT | 78.9 | 78.9 | — | 111% |
| | 1:2 | 41.0 | 82.0 | 104% | |
| | 1:3 | 30.9 | 92.7 | 118% | |
| | 1:4 | 22.2 | 88.8 | 112% | |
| 816 | neat | 88.2 | 88.2 | — | 109% |
| | 1:2 | 45.1 | 90.2 | 102% | |
| | 1:3 | 33.0 | 99.0 | 112% | |
| | 1:4 | 24.6 | 98.4 | 112% | |
| 817 | neat | 144.6 | 144.6 | — | 118% |
| | 1:2 | 75.5 | 151.0 | 104% | |
| | 1:3 | 55.1 | 165.3 | 114% | |
| | 1:4 | 43.1 | 172.4 | 119% | |
| | 1:6 | 32.7 | 196.2 | 136% | |
| 830 | neat | 77.5 | 77.5 | — | 120% |
| | 1:2 | 43.1 | 86.2 | 111% | |
| | 1:3 | 29.9 | 89.7 | 116% | |

TABLE 2-continued

| SAMPLE | DILU-TION | U/M1 MEAS-URED | U/M1 CO-RRECTED | RECOV-ERY | AVERAGE RECOVERY |
|---|---|---|---|---|---|
| | 1:4 | 26.0 | 104.0 | 134% | |
| 832 | neat | 81.5 | 81.5 | — | 112% |
| | 1:2 | 51.6 | 103.2 | 127% | |
| | 1:3 | 26.3 | 78.9 | 96.8% | |
| | 1:4 | 22.6 | 90.4 | 111% | |
| 883 | neat | 75.4 | 75.4 | — | 113% |
| | 1:2 | 40.2 | 80.4 | 107% | |
| | 1:3 | 30.4 | 91.2 | 121% | |
| | 1:4 | 21.1 | 84.4 | 112% | |
| 884 | neat | 56.7 | 56.7 | — | 101% |
| | 1:2 | 30.3 | 60.0 | 106% | |
| | 1:3 | 18.8 | 56.4 | 99.5% | |
| | 1:4 | 13.9 | 55.6 | 98.0% | |
| 886 | neat | 65.5 | 65.5 | — | 113% |
| | 1:2 | 35.6 | 71.2 | 109% | |
| | 1:3 | 25.7 | 77.1 | 118% | |
| | 1:4 | 18.3 | 73.2 | 112% | |
| 888 | neat | 68.1 | 68.1 | — | 114% |
| | 1:2 | 40.3 | 80.6 | 118% | |
| | 1:3 | 25.8 | 77.4 | 114% | |
| | 1:4 | 18.5 | 74.0 | 109% | |
| 891 | neat | 97.6 | 97.6 | — | 103% |
| | 1:2 | 54.3 | 108.6 | 111% | |
| | 1:3 | 33.0 | 99.0 | 101% | |
| | 1:4 | 23.7 | 94.8 | 97.1% | |
| 896 | neat | 127.8 | 127.8 | — | 116% |
| | 1:2 | 72.0 | 144.0 | 113% | |
| | 1:3 | 48.8 | 146.4 | 115% | |
| | 1:4 | 35.5 | 142.0 | 111% | |
| | 1:6 | 26.7 | 160.2 | 125% | |
| | 1:8 | 18.2 | 145.6 | 114% | |

Example 5

CD4 TRAx™ Paper Dot Assay-Intrassay Precision

Within one assay, 10 samples are assayed in triplicate (i.e., 3 spots for each sample), with the results as shown in Table 3. The average correlation value (CV) for the triplicate (spots) of the above 10 samples is 4.1%.

TABLE 3

| SAMPLE | 1 | 2 | 3 | AVE. n = 3 | CV n = 3 |
|---|---|---|---|---|---|
| 772 | 67.1 | 64.7 | 67.7 | 66.5 | 2.4% |
| 773 | 47.4 | 46.7 | 45.1 | 46.4 | 2.5% |
| 774 | 69.2 | 66.8 | 69.9 | 68.6 | 2.3% |
| 775 | 89.6 | 93.4 | 102.7 | 95.2 | 7.1% |
| 776 | 47.9 | 45.8 | 44.4 | 46.0 | 3.8% |
| 777 | 54.7 | 52.1 | 54.7 | 53.8 | 2.7% |
| 778 | 37.4 | 39.2 | 41.9 | 39.5 | 5.8% |
| 779 | 66.8 | 68.5 | 67.5 | 67.6 | 1.3% |
| 780 | 48.6 | 53.9 | 53.6 | 52.0 | 5.8% |
| 781 | 90.4 | 95.4 | 105.3 | 97.0 | 7.8% |

Example 6

CD4 TRAx™ Paper Dot Assay-Interassay Variation

Four samples were assayed for interassay variation. The results are shown in Table 4.

TABLE 4

| DATE | SAMPLE 997 | SAMPLE 998 | SAMPLE 1000 | SAMPLE 1001 |
|---|---|---|---|---|
| 3/16/93 | 105.6 | 87.0 | 101.5 | 76.9 |
| 3/17/93 | 106.1 | 76.7 | 99.3 | 84.3 |
| 3/18/93 | 108.4 | 74.4 | 102.8 | 76.8 |
| 3/19/93 | 110.6 | 74.1 | 98.4 | 80.1 |
| 3/23/93 | 91.0 | 71.0 | 95.8 | 77.2 |
| 3/23/93 | 97.5 | 75.2 | 93.4 | 71.9 |
| 3/25/93 | 120.6 | 80.7 | 100.8 | 81.9 |
| 3/26/93 | 109.5 | 80.9 | 99.5 | 83.2 |
| 3/30/93 | 101.5 | 74.2 | 94.2 | 75.9 |
| 3/30/93 | 100.3 | 79.7 | 92.2 | 72.3 |
| 3/31/93 | 109.6 | 75.4 | 93.9 | 76.1 |
| 3/31/93 | 98.9 | 65.4 | 92.9 | 73.9 |
| 4/02/93 | 97.2 | 67.6 | 94.3 | 73.5 |
| 4/06/93 | 116.5 | 73.9 | 97.9 | 85.6 |
| 4/07/93 | 102.8 | 72.5 | 90.6 | 79.5 |
| 4/08/93 | 113.6 | 81.7 | 95.8 | 77.0 |
| 4/13/93 | 106.2 | 86.5 | 95.6 | 73.0 |
| 4/16/93 | 114.3 | 76.6 | 88.9 | 77.1 |
| 4/20/93 | 107.3 | 72.7 | 98.8 | — |
| 4/20/93 | — | 79.0 | — | — |

An average CV of 5.9 was determined as follows:

| sample n | | mean | SD | CV |
|---|---|---|---|---|
| 997 | 19 | 106.2 | 7.4 | 7.0 |
| 998 | 20 | 76.3 | 5.5 | 7.2 |
| 1000 | 19 | 96.1 | 3.8 | 4.0 |
| 1001 | 18 | 77.6 | 4.1 | 5.3 |

Example 7

CD4 TRAx™ Paper Dot Assay-Correlation of Dried Blood Specimens to Lysate

Figure 1:
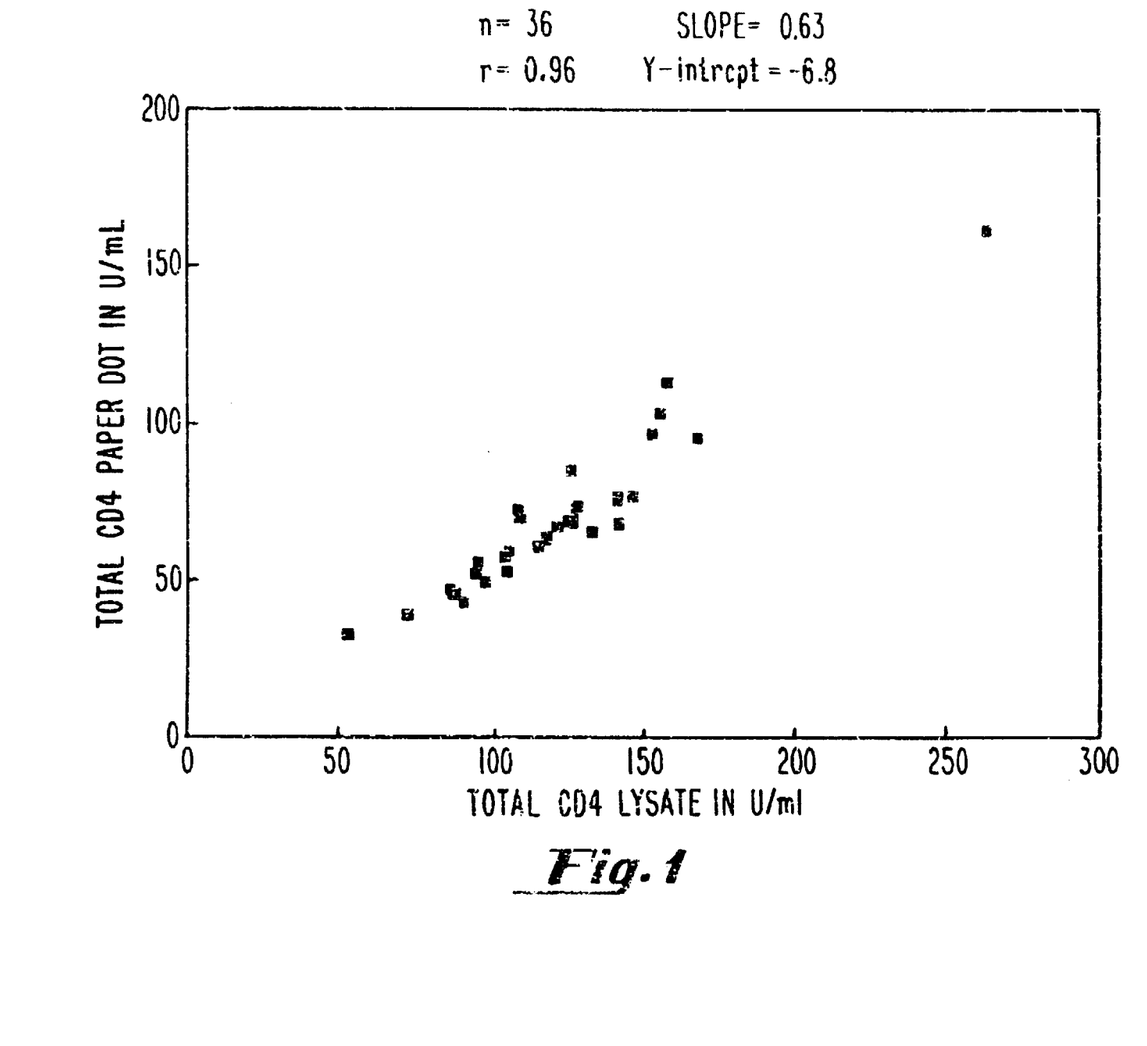
FIG. 1 is a graph showing the correlation of dried blood specimens to lysate in a CD4 TRAx™ assay. CD4 dried blood specimens values are in units per ml (U/ml). A unit is defined as the amount of CD4 found in $10^3$ Jurkat cells lysed with 1% NP-40.

The correlation of dried blood specimens to lysate was determined. The results are shown in Table 5 and FIG. 1.

TABLE 5

| SAMPLE | DBS (U/M1) | LYSATE (U/M1) |
|---|---|---|
| 762 | 45.9 | 86.8 |
| 763 | 64.9 | 116.9 |
| 764 | 69.4 | 124.5 |
| 765 | 43.9 | 91.3 |
| 766 | 60.4 | 105.2 |
| 767 | 74.8 | 128.0 |
| 768 | 75.3 | 141.6 |
| 769 | 63.0 | 118.4 |
| 770 | 61.4 | 114.8 |
| 771 | 49.3 | 97.3 |
| 772 | 66.5 | 133.3 |
| 773 | 46.4 | 89.0 |
| 774 | 68.6 | 141.7 |
| 775 | 95.2 | 167.9 |
| 776 | 46.0 | 89.4 |
| 777 | 53.8 | 104.0 |
| 778 | 39.5 | 71.8 |
| 779 | 67.6 | 120.5 |
| 780 | 52.0 | 93.6 |
| 781 | 97.0 | 168.2 |
| 783 | 56.3 | 94.6 |
| 784 | 68.6 | 126.0 |
| 785 | 77.4 | 141.8 |
| 786 | 33.4 | 53.5 |
| 787 | 47.9 | 85.8 |
| 798 | 72.4 | 127.5 |
| 815 | 72.6 | 108.1 |
| 816 | 103.4 | 155.2 |

TABLE 5-continued

| SAMPLE | DBS (U/Ml) | LYSATE (U/Ml) |
|---|---|---|
| 817 | 162.0 | 263.7 |
| 818 | 71.1 | 108.4 |
| 830 | 97.7 | 152.9 |
| 831 | 85.7 | 126.0 |
| 832 | 113.2 | 157.5 |
| 833 | 33.5 | 52.2 |
| 758 | 77.3 | 146.6 |
| 759 | 58.3 | 103.8 |

Example 8

CD4 TRAx™ Paper Dot Assay-Correlation of Dried Blood Spots to Flow Cytometry

The correlation of dried blood specimen results to that obtained with flow cytometry was determined. The results are shown in Table 6 and FIG. 2.

TABLE 6

| SAMPLE | DBS U/Ml | FLOW ABS.CD4 cells/U1 | WBL U/Ml |
|---|---|---|---|
| 762 | 45.9 | 681 | 86.3 |
| 763 | 64.9 | 941 | 116.9 |
| 764 | 69.4 | 1218 | 124.5 |
| 765 | 43.9 | 839 | 91.3 |
| 766 | 60.4 | 764 | 105.2 |
| 767 | 74.8 | 1097 | 128 |
| 768 | 75.3 | 1292 | 141.6 |
| 769 | 63.0 | 1165 | 118.4 |
| 770 | 61.4 | 921 | 114.8 |
| 771 | 49.3 | 771 | 97.3 |
| 772 | 66.0 | 1037 | 133.3 |
| 773 | 45.4 | 631 | 89 |
| 774 | 66.9 | 1126 | 141.7 |
| 775 | 90.8 | 1397 | 167.9 |
| 776 | 46.0 | 715 | 89.4 |
| 777 | 51.2 | 843 | 104 |
| 778 | 38.6 | 524 | 71.8 |
| 779 | 64.0 | 1135 | 120.5 |
| 780 | 49.6 | 713 | 93.6 |
| 781 | 93.8 | 1567 | 168.2 |
| 783 | 55.4 | 590 | 94.6 |
| 784 | 73.2 | 1200 | 126 |
| 785 | 76.4 | 1347 | 141.8 |
| 786 | 33.8 | 421 | 53.5 |
| 787 | 47.9 | 1025 | 85.8 |
| 798 | 72.4 | 1058 | 127.5 |
| 815 | 72.6 | 920 | 108.1 |
| 816 | 103.4 | 1731 | 155.2 |
| 817 | 162.0 | 2408 | 263.7 |
| 818 | 71.1 | 11.02 | 108.4 |
| 821 | 64.6 | 657 | 105.3 |
| 823 | 76.7 | 1058 | 118.4 |
| 824 | 84.3 | 1126 | 136.6 |

Figure 2:
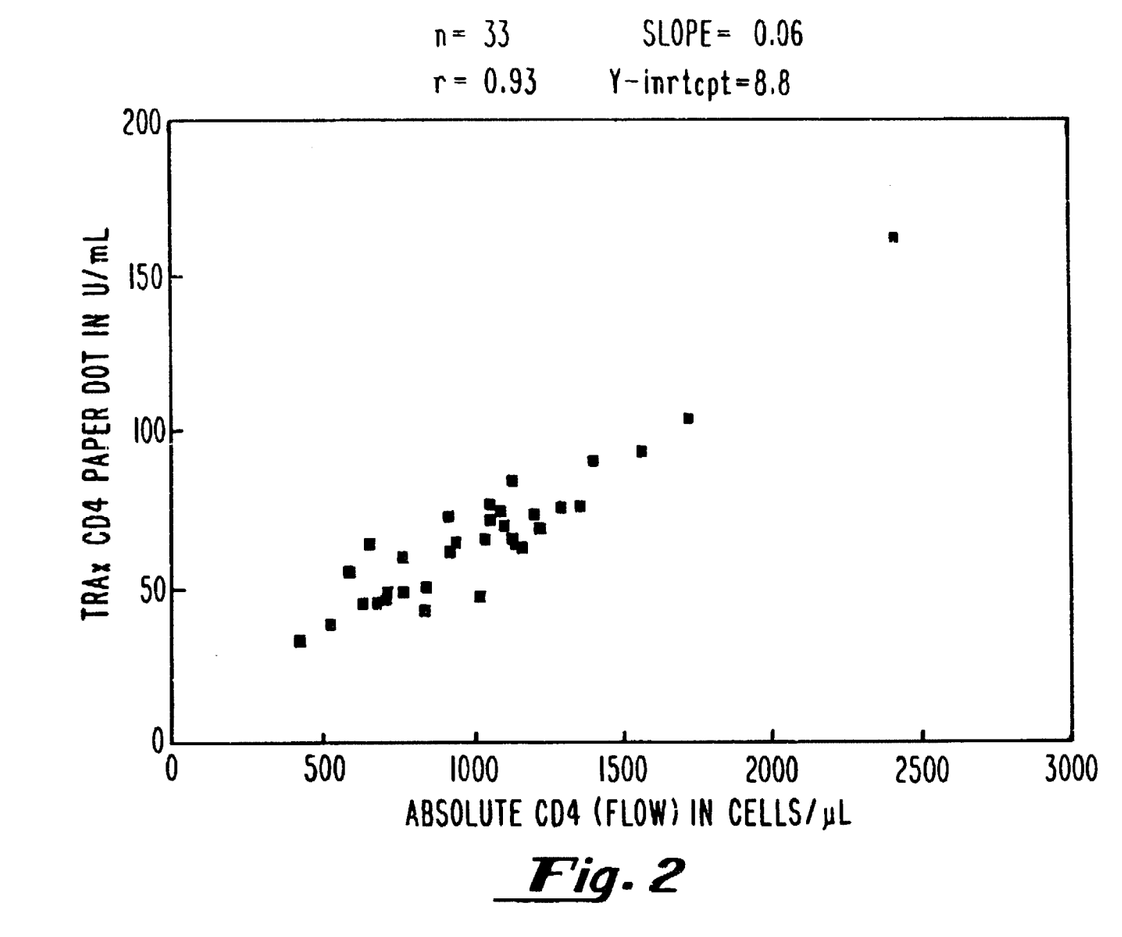
FIG. 2 is a graph showing the correlation of dried blood specimens in a CD4 TRAx™ assay to flow cytometry. CD4 dried blood specimens values are in units per ml (U/ml). A unit is defined as the amount of CD4 found in $10^3$ Jurkat cells lysed with 1% NP-40. The conversion of U/ml to equivalent CD4 count is based upon the linear relationship established between U/ml and CD4 cell count as determined by flow cytometry. Data from clinical studies of patients with a broad range of CD4 levels was used to derive the conversion equation. The values for the standards for the TRAx™ assay kit are calibrated to CD4 T lymphocytes and specimen results are read directly from the standard curve and reported as cell/µ l.

A correlation of 0.93 was found as shown in FIG. 2.

What is claimed is:

1. A method for measuring the amount of a cell-associated molecule in a sample from a subject comprising the steps of:

(a) spotting and drying a selected amount of a liquid biological sample from a subject onto a filter paper collection device to produce a stable, dried biological sample spot which can be stored;

(b) contacting the filter paper collection device with the dried biological sample spot with a selected diluent and lysis reagent for a selected period of time at a selected temperature to produce a solubilized sample;

(c) recovering a selected amount of said solubilized sample;

(d) contacting said solubilized sample with at least one binding partner specific for a cell-associated molecule under conditions which allow specific binding; and (e) measuring the amount of any specific binding that occurs of a component in the sample with said at least one binding partner, wherein the amount of specific binding indicates the amount of the cell-associated molecule in the sample, wherein the cell associated molecule being measured is selected from the group consisting of CD4, CD8, CD3, CD19, CD2 and CD54.

2. The method of claim 1 wherein said cell-associated molecule is CD4.

3. The method of claim 1 wherein said selected diluent comprises a buffer and lysis reagent.

4. The method of claim 1 wherein said selected lysis reagent comprises a non-ionic detergent.

5. The method of claim 1 wherein the filter paper collection device is contacted with the diluent and lysis reagent for at least 2 hours at about room temperature.

6. The method of claim 1 wherein said selected amount of solubilized sample comprises 50 µl.

7. The method of claim 1 wherein the liquid biological fluid is blood which is spotted onto the filter paper collection device and dried to produce a dried blood spot.

8. The method of claim 7 wherein a 0.25 inch diameter portion of the dried blood spot is removed.

9. The mether of claim 7 wherein said 0.25 inch diameter portion is then contacted with the diluent and lysis reagent in step (b).

10. The method of claim 1 wherein said filter paper collection device comprises grade 903 filter paper having circular markings indicated thereupon.

11. The method of claim 10 wherein said circular markings are capable of containing about 60 µl of blood.

12. The method of claim 1 wherein said liquid biological sample is selected from the group consisting of saliva, urine, pleural effusions, tissue infiltrates, spinal fluid, synovial fluid, and blood.

* * * * *

UNITED STATES PATENT AND TRADEMARK OFFICE
CERTIFICATE OF CORRECTION

PATENT NO. : 5,747,265

DATED : May 5, 1998

INVENTOR(S) : Parsons et al.

It is certified that error appears in the above-indentified patent and that said Letters Patent is hereby corrected as shown below:

In the Abstract, please delete "A dot is punched form the dried blood" and insert therefor --A dot is punched from the dried blood--.

At col 5, line 35, please delete "wee" and insert therefor --were--.

At col 7, line 17, please delete "form" and insert therefor --from--.

At col 8, line 3 , please delete "the" and insert therefor --The--.

At col 9, line 6, please delete "st" and insert therefor --at--.

In claim 9, please delete "mether" and insert therefor --method--.

Signed and Sealed this

Twenty-fifth Day of August, 1998

Attest:

BRUCE LEHMAN

Attesting Officer

Commissioner of Patents and Trademarks